(12) United States Patent
Miyaki et al.

(10) Patent No.: US 12,376,830 B2
(45) Date of Patent: Aug. 5, 2025

(54) MEDICAL IMAGE DIAGNOSIS APPARATUS, MEDICAL INFORMATION PROCESSING APPARATUS, AND MEDICAL IMAGE PROCESSING METHOD

(71) Applicant: CANON MEDICAL SYSTEMS CORPORATION, Otawara (JP)

(72) Inventors: Keisuke Miyaki, Utsunomiya (JP); Yasunori Honjo, Utsunomiya (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 613 days.

(21) Appl. No.: 17/658,964

(22) Filed: Apr. 12, 2022

(65) Prior Publication Data

US 2022/0330921 A1    Oct. 20, 2022

(30) Foreign Application Priority Data

Apr. 16, 2021 (JP) ................. 2021-069980

(51) Int. Cl.
*A61B 8/00* (2006.01)
*A61B 8/08* (2006.01)
(Continued)

(52) U.S. Cl.
CPC .......... *A61B 8/5215* (2013.01); *A61B 8/0883* (2013.01); *A61B 8/461* (2013.01);
(Continued)

(58) Field of Classification Search
CPC ..... A61B 8/5215; A61B 8/0883; A61B 8/461; G06T 7/70; G06T 11/003;
(Continued)

(56) References Cited

U.S. PATENT DOCUMENTS 6,245,017 B1 *  6/2001  Hashimoto ............. A61B 8/06
                                                        600/447
6,572,547 B2 *  6/2003  Miller ................. A61B 8/4483
                                                        600/459
(Continued)

FOREIGN PATENT DOCUMENTS

JP    2007-229302 A        9/2007
JP    2019-38098  A   *    3/2019 .............. A61B 8/14
JP    2020-81303  A        6/2020

OTHER PUBLICATIONS

Japanese Office Action issued Sep. 3, 2024 in Japanese Patent Application No. 2021-069980, 2 pages.

*Primary Examiner* — Shefali D Goradia

(74) *Attorney, Agent, or Firm* — Oblon, McClelland, Maier & Neustadt, L.L.P.

(57) ABSTRACT

A medical image diagnosis apparatus according to an embodiment includes a processing circuit. The processing circuit is configured to obtain three-dimensional data related to a target site. The processing circuit is configured to generate a three-dimensional model of the target site by using the obtained three-dimensional data. The processing circuit is configured to calculate positions of one or more recommended cross-sections to be set for the target site, on the basis of information about the size of the target site obtained by using the three-dimensional model. The processing circuit is configured to cause a display device to display the positions of the one or more recommended cross-sections.

10 Claims, 7 Drawing Sheets

(51) Int. Cl.
*G06T 7/70* (2017.01)
*G06T 11/00* (2006.01)
G06T 7/73 (2017.01)
G06T 11/60 (2006.01)

(52) U.S. Cl.
CPC .............. *G06T 7/70* (2017.01); *G06T 11/003* (2013.01); *G06T 7/75* (2017.01); *G06T 11/60* (2013.01); *G06T 2207/10136* (2013.01); *G06T 2207/30048* (2013.01); *G06T 2210/41* (2013.01)

(58) Field of Classification Search
CPC . G06T 2207/10136; G06T 2207/30048; G06T 2210/41
See application file for complete search history.

(56) References Cited

U.S. PATENT DOCUMENTS

| | | | |
|---|---|---|---|
| 10,674,994 B2 * | 6/2020 | Zhu | A61B 8/483 |
| 11,508,104 B2 * | 11/2022 | Miyaki | A61B 8/0841 |
| 2007/0239021 A1 | 10/2007 | Oonuki et al. | |
| 2013/0231564 A1 * | 9/2013 | Zagorchev | G06T 7/62 |
| | | | 600/447 |
| 2015/0038846 A1 * | 2/2015 | Abe | A61B 8/14 |
| | | | 600/443 |

\* cited by examiner

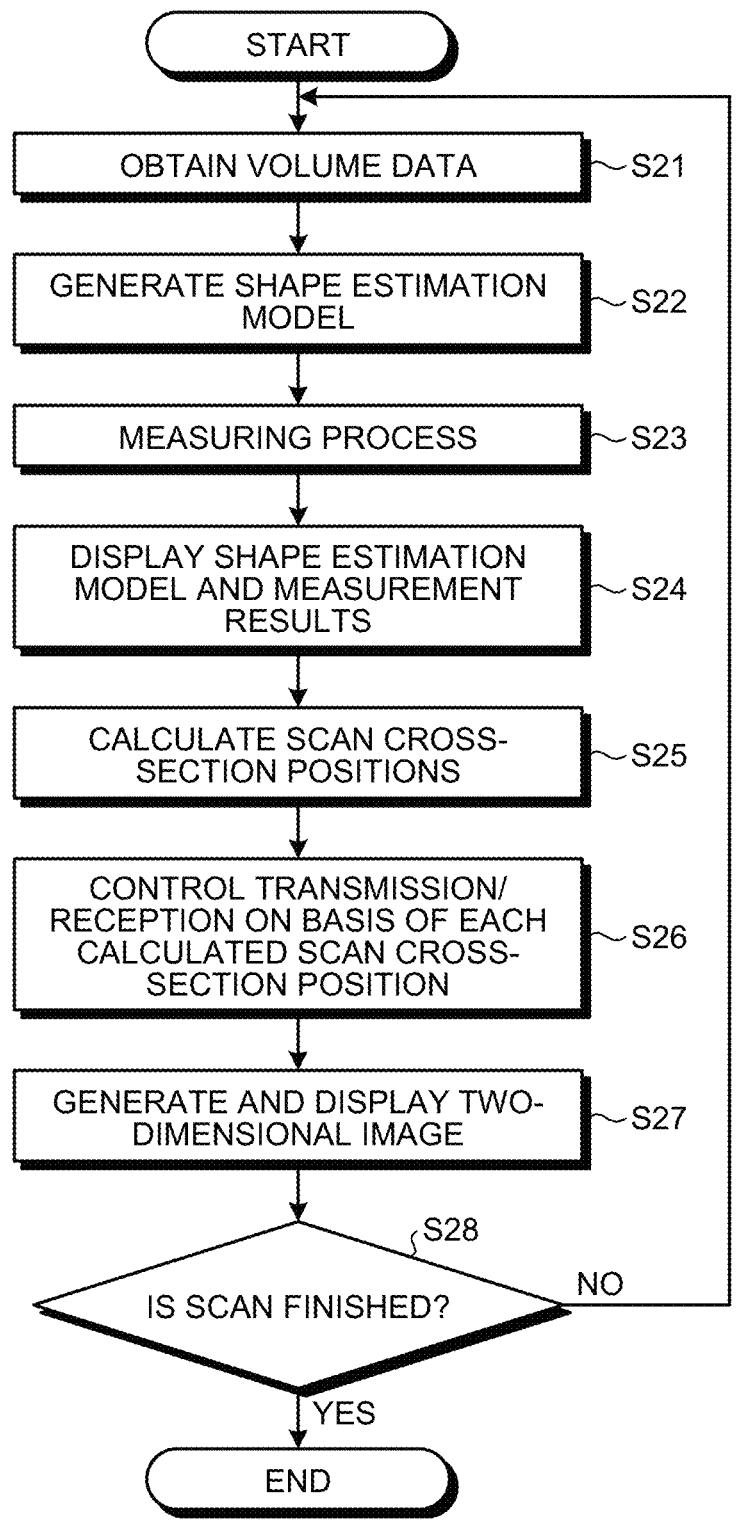

MEDICAL IMAGE DIAGNOSIS APPARATUS, MEDICAL INFORMATION PROCESSING APPARATUS, AND MEDICAL IMAGE PROCESSING METHOD

CROSS-REFERENCE TO RELATED APPLICATIONS

This application is based upon and claims the benefit of priority from Japanese Patent Application No. 2021-069980, filed on Apr. 16, 2021; the entire contents of which are incorporated herein by reference.

FIELD

Embodiments described herein relate generally to a medical image diagnosis apparatus, medical information processing apparatus, and a medical image processing method.

BACKGROUND

For example, one of typical treatment methods for reducing risk of cerebral apoplexy caused by atrial fibrillation is a method called transcatheter left atrial appendage closure using a left atrial appendage closure device. The transcatheter left atrial appendage closure denotes a treatment method by which the left atrial appendage closure device is placed in an entrance part of the left atrial appendage (hereinafter, "left atrial appendage entrance part") with the use of a catheter. During a transcatheter left atrial appendage closure process, it is necessary to accurately learn the shapes of the left atrial appendage entrance part and the surrounding site thereof, in order to determine specifications as to the size of the left atrial appendage closure device. Conventionally, for example, the shapes of the left atrial appendage entrance part and the surrounding site thereof are measured by using ultrasound images on four cross-sections obtained by using a transesophageal probe.

According to the conventional method, however, it is necessary to promptly and correctly set, through a manual operation, the four cross-sections used for the shape measuring purpose. Accordingly, there is a large workload imposed on the operator. Further, because the two-dimensional ultrasound images are used, the precision level of the measuring process may not be sufficient in some situations.

BRIEF DESCRIPTION OF THE DRAWINGS

FIG. 8 is a flowchart illustrating an example of a flow in left atrial appendage closure aiding processes including the recommended cross-section position calculating process according to the embodiment.

DETAILED DESCRIPTION

A medical image diagnosis apparatus according to an embodiment includes a processing circuit. The processing circuit is configured to obtain three-dimensional data related to a target site. The processing circuit is configured to generate a three-dimensional model of the target site by using the obtained three-dimensional data. The processing circuit is configured to calculate positions of one or more recommended cross-sections to be set for the target site, on the basis of information about the size of the target site obtained by using the three-dimensional model. The processing circuit is configured to cause a display device to display the positions of the one or more recommended cross-sections.

In the following sections, exemplary embodiments of an ultrasound diagnosis apparatus will be explained in detail, with reference to the accompanying drawings. To explain specific examples, the following will describe examples in which the left atrial appendage serves as a diagnosed site.

Figure 1:
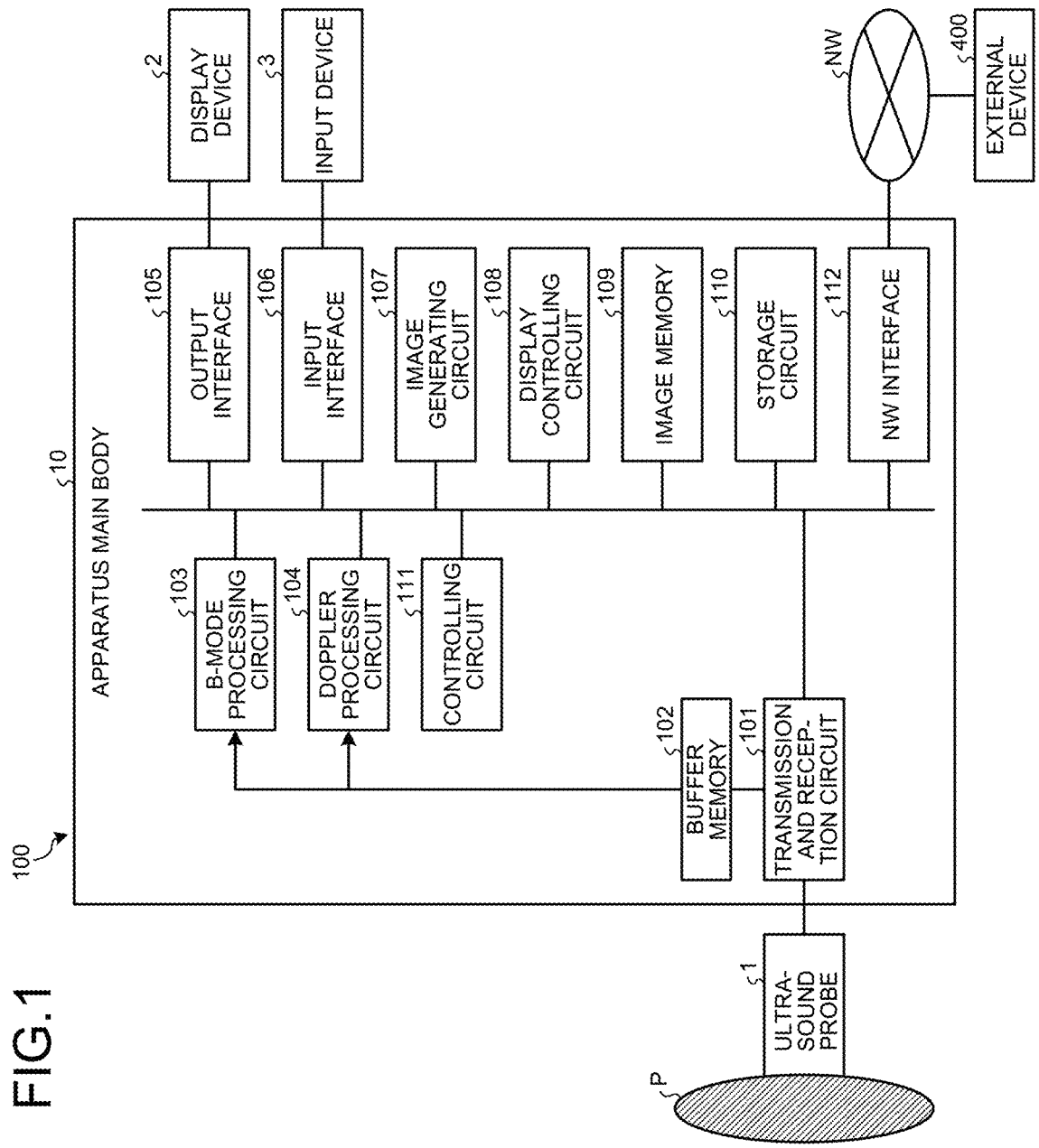
FIG. 1 is a block diagram illustrating an example of an ultrasound diagnosis apparatus according to an embodiment.

FIG. 1 is a block diagram illustrating an example of an ultrasound diagnosis apparatus 100 according to an embodiment. As illustrated in FIG. 1, the ultrasound diagnosis apparatus 100 includes an apparatus main body 10, an ultrasound probe 1, an input device 3, and a display device 2.

The apparatus main body 10 includes a transmission and reception circuit 101, a buffer memory 102, a B-mode processing circuit 103, a Doppler processing circuit 104, an output interface 105, an input interface 106, an image generating circuit 107, a display controlling circuit 108, an image memory 109, a storage circuit 110, a controlling circuit 111, and a network (NW) interface 112. Further, the apparatus main body 10 is connected to an external device 400 via a network NW.

The ultrasound probe 1 includes a plurality of elements such as piezoelectric transducer elements, for example. The plurality of elements are configured to generate an ultrasound wave on the basis of a drive signal supplied from the transmission and reception circuit 101 included in the apparatus main body 10. Further, the ultrasound probe 1 is configured to receive a reflected wave from an examined subject (hereinafter, "patient") P and to convert the reflected wave into an electrical signal. Further, the ultrasound probe 1 includes, for example, a matching layer provided for the piezoelectric transducer elements, a backing member that prevents the ultrasound wave from propagating rearward from the piezoelectric transducer elements, and the like. In this situation, the ultrasound probe 1 is detachably connected to the apparatus main body 10.

When an ultrasound wave is transmitted from the ultrasound probe 1 to the patient P, the transmitted ultrasound wave is repeatedly reflected on a surface of discontinuity of acoustic impedances at a tissue in the body of the patient P and is received as a reflected-wave signal by the plurality of elements included in the ultrasound probe 1. The amplitude of the received reflected-wave signal is dependent on the difference between the acoustic impedances on the surface of discontinuity on which the ultrasound wave is reflected.

Further, when a transmitted ultrasound pulse is reflected on the surface of a moving blood flow, a cardiac wall, or the like, the reflected-wave signal is, due to the Doppler effect, subject to a frequency shift, depending on a velocity component of the moving members with respect to the ultrasound wave transmission direction. Further, the ultrasound probe 1 is configured to output the reflected-wave signal to the transmission and reception circuit 101 of the apparatus main body 10.

It is assumed that the ultrasound probe 1 according to the present embodiment is a transesophageal probe. In the present example, the transesophageal probe is a probe configured to perform an ultrasound scan on the heart or the like from the inside of the body (the esophagus) after being inserted through the nose or the mouth to be placed in the esophagus. Further, in the present embodiment, it is assumed that the transesophageal probe is a two-dimensional array probe (a probe having, at the tip end thereof, a plurality of ultrasound transducer elements arranged in a two-dimensional matrix formation) capable of obtaining volume data. Other examples of the transesophageal probe besides the two-dimensional array probe include a mechanical probe capable of performing an ultrasound scan on an arbitrary cross-section, by mechanically rotating a one-dimensional array probe in which a plurality of ultrasound transducer elements are arranged along a predetermined direction. An example using a mechanical probe as the ultrasound probe 1 will be explained as a second modification example.

For example, the input device 3 is realized by using input means such as a mouse, a keyboard, a button, a panel switch, a touch command screen, a foot switch, a trackball, a joystick, and/or the like. The input device 3 is configured to receive various types of setting requests from an operator of the ultrasound diagnosis apparatus 100 and to transfer the received various types of setting requests to the apparatus main body 10. For example, instructions related to starting up or ending recommended cross-section aiding functions (explained later) are input via the input device 3.

For example, the display device 2 is configured to display a Graphical User Interface (GUI) used by the operator of the ultrasound diagnosis apparatus 100 for inputting the various types of setting requests through the input device 3 and to display an ultrasound image represented by ultrasound image data generated by the apparatus main body 10, or the like. The display device 2 is realized by using a liquid crystal monitor, a Cathode Ray Tube (CRT) monitor, or the like. The display device 2 is an example a display unit.

Under control of the controlling circuit 111, the transmission and reception circuit 101 is configured to cause an ultrasound wave to be transmitted from the ultrasound probe 1 and to cause the ultrasound probe 1 to receive an ultrasound wave (the reflected wave of the ultrasound wave). In other words, the transmission and reception circuit 101 is configured to perform an ultrasound scan (a scan using the ultrasound wave) via the ultrasound probe 1.

More specifically, under the control of the controlling circuit 111, the transmission and reception circuit 101 is configured to cause the ultrasound probe 1 to transmit the ultrasound wave. For example, the transmission and reception circuit 101 includes a trigger generating circuit, a delay circuit, a pulse circuit, and the like (not illustrated). The trigger generating circuit is configured to repeatedly generate a trigger pulse for forming a transmission ultrasound wave at a predetermined rate frequency fr Hz. Further, the delay circuit is configured to apply a delay time period required to converge the ultrasound wave into the form of a beam for each channel and to determine transmission directionality, to each of the trigger pulses. With the timing based on the trigger pulses, the pulser circuit is configured to apply a drive pulse to the ultrasound probe 1.

Further, the transmission and reception circuit 101 is configured to generate reflected-wave ultrasound data, which is ultrasound data based on the reflected-wave signal received by the ultrasound probe 1. Further, the transmission and reception circuit 101 is configured to store the generated reflected-wave ultrasound data into the buffer memory 102.

More specifically, after reaching the piezoelectric transducer elements inside the ultrasound probe 1, the reflected wave of the ultrasound wave transmitted by the ultrasound probe 1 is converted from mechanical vibration into the electrical signal (the reflected-wave signal) at the piezoelectric transducer elements, so as to be input to the transmission and reception circuit 101. For example, the transmission and reception circuit 101 includes a pre-amplifier, an Analog to Digital (A/D) converter, a quadrature detection circuit, and the like and is configured to generate the reflected-wave ultrasound data by performing various types of processes on the reflected-wave signal received by the ultrasound probe 1. In the present embodiment, "obtaining ultrasound data" includes obtaining ultrasound data by transmitting and receiving an ultrasound wave. The transmission and reception circuit 101 is an example of an obtaining unit according to the present embodiment.

The reflected-wave data is two-dimensional data in which a plurality of pieces of data at a plurality of sampling points arranged along a depth direction on each of the scanning lines (which hereinafter may be referred to as "raster lines") are arranged along the raster line direction in a quantity equal to the number of raster lines.

The pre-amplifier is configured to amplify the reflected-wave signal for each channel and to adjust gain thereof (a gain correction). The A/D converter is configured to convert the gain-corrected reflected-wave signal into a digital signal, by performing an A/D conversion on the gain-corrected reflected-wave signal. The quadrature detection circuit is configured to convert the reflected-wave signal resulting from the A/D conversion into an In-phase signal (an I signal) and a quadrature-phase signal (a Q signal) in a baseband.

Further, the quadrature detection circuit is configured to store the I signal and the Q signal into the buffer memory 102, as the reflected-wave ultrasound data. In the following sections, when being collectively referred to, the I signal and the Q signal will be referred to as IQ signals. Further, because the IQ signals represent the digital data resulting from the A/D conversion, the IQ signals may be referred to as IQ data.

The buffer memory 102 is configured to at least temporarily store therein the reflected-wave ultrasound data (the IQ data) generated by the transmission and reception circuit 101. For example, the buffer memory 102 is configured to store therein the reflected-wave ultrasound data obtained by performing the ultrasound transmission/reception multiple times per raster line. In this situation, by performing the ultrasound transmission/reception multiple times per raster line, a plurality of pieces of reflected-wave ultrasound data corresponding to the same raster line are obtained. In the following sections, the number of pieces of reflected-wave ultrasound data corresponding to mutually the same raster line will be referred to as an ensemble number, whereas the data itself will be referred to as ensemble data. The buffer memory 102 is configured to store therein, sequentially in the raster order, pieces of ensemble data arranged in the time direction in a quantity equal to the ensemble number. For example, the buffer memory 102 is realized by using a semiconductor memory element such as a Random Access Memory (RAM) or a flash memory.

The B-mode processing circuit 103 is configured to generate data (B-mode data) in which signal intensities are expressed as levels of brightness, by performing a logarithmic amplifying process, an envelope detecting process, a logarithmic compressing process, and/or the like on the reflected-wave ultrasound data read from the buffer memory 102.

The Doppler processing circuit 104 is configured to generate data (Doppler data) obtained by extracting movement information based on the Doppler effect, with respect to a moving member present in a Region Of Interest (ROI) being set in a scan region, by performing a frequency analysis on the reflected-wave ultrasound data stored in the buffer memory 102. The moving member may be blood, for example. For instance, the Doppler processing circuit 104 is capable of implementing a color Doppler method, which may also be called a Color Flow Mapping (CFM) method.

The ultrasound probe 1, the transmission and reception circuit 101, and the B-mode processing circuit 103 are each an example of an obtaining unit.

The output interface 105 is configured to output an electrical signal from the controlling circuit 111 to the outside. For example, the output interface 105 is connected to the controlling circuit 111 via a bus and is configured to output the electrical signal from the controlling circuit 111 to the display device 2.

Via the input device 3, the input interface 106 is configured to receive various types of instructions from the operator. For example, the input interface 106 is connected to the controlling circuit 111 via a bus and is configured to convert an operation instruction input by the operator into an electrical signal and to output the electrical signal to the controlling circuit 111. In this situation, the input interface 106 does not necessarily have to be connected to physical operation component parts such as a mouse and/or a keyboard. For instance, possible examples of the input interface include a circuit configured to receive an electrical signal corresponding to an operation instruction input from an external input device provided separately from the ultrasound diagnosis apparatus 100 and to output the electrical signal to the controlling circuit 111.

On the basis of the data generated by the B-mode processing circuit 103 and the Doppler processing circuit 104, the image generating circuit 107 is configured to generate two-dimensional ultrasound image data (hereinafter, "two-dimensional image data" or "slice data") and three-dimensional ultrasound image data (hereinafter, "three-dimensional data" or "volume data"). The image generating circuit 107 is configured to store the generated ultrasound image data into the image memory 109.

More specifically, on the basis of the B-mode data generated by the B-mode processing circuit 103, the image generating circuit 107 is configured to generate B-mode image data that is either two-dimensional or three-dimensional.

On the basis of the Doppler data generated by the Doppler processing circuit 104, the image generating circuit 107 is configured to generate Doppler image data that is either two-dimensional or three-dimensional. The Doppler image data is an example of blood flow image data according to the present embodiment. The image generating circuit 107 is configured to generate the Doppler image data on the basis of intensity information and phase change information included in the Doppler data generated by the Doppler processing circuit 104.

The image generating circuit 107 is configured to generate a two-dimensional image corresponding to an arbitrary cross-section, by performing a Multi Planar Reconstruction (MPR) process using volume data. In the present embodiment, an image obtained by performing the MPR process will be referred to as an MPR image.

Further, the image generating circuit 107 is configured to perform a process (hereinafter, "shape estimation model generating process") of generating a shape estimation model by using volume data. By using the generated shape estimation model, the image generating circuit 107 is configured to perform a measuring process (hereinafter, "target site size measuring process") related to the size of a target site. On the basis of a result of the target site size measuring process, the image generating circuit 107 is configured to perform a process (hereinafter, "recommended cross-section position calculating process") of calculating the position of at least one recommended cross-section.

In this situation, the recommended cross-section denotes a cross-section desirable for imaging and observing the target site for the purpose of a diagnosing process, surgery, or the like. It is possible to anatomically determine the position of the recommended cross-section on the basis of the size, the shape, and/or the like of the target site, for example.

Further, on the basis of a result of the target site size measuring process, the image generating circuit 107 is configured to perform a process (hereinafter, "device size determining process") of determining the size of a device to be used for treatment or surgery of the target site.

The shape estimation model generating process, the target site size measuring process, the recommended cross-section position calculating process, and the device size determining process will be explained in detail later.

The display controlling circuit 108 is configured to cause the display device 2 to display an ultrasound image based on any of the various types of ultrasound image data generated by the image generating circuit 107. The display controlling circuit 108 is configured to cause the display device 2 to display the position of at least one recommended cross-section. The display controlling circuit 108 is configured to cause the display device 2 to display the shape estimation model obtained from the shape estimation model generating process, measurement results from the target site size measuring process, a calculation result from the recommended cross-section position calculating process, and a determination result from the device size determining process. Further, the display controlling circuit 108 may also cause the display device 2 to display the GUI used by the operator to input the various types of setting requests through the input device 3. The display controlling circuit 108 is an example of a display controlling unit.

The image memory 109 is configured to store therein various types of image data generated by the controlling circuit 111. For example, the image memory 109 is realized by using a semiconductor memory element such as a RAM or a flash memory, or a hard disk, an optical disk, or the like.

For example, the storage circuit 110 is realized by using a magnetic or optical storage medium, a semiconductor memory element such as a flash memory, or a storage medium that can be read by a processor such as a hard disk or an optical disk. The storage circuit 110 has stored therein a program for realizing the ultrasound transmission/reception, various types of data, and the like.

Further, the storage circuit 110 has stored therein a table keeping information about sizes of the left atrial appendage in correspondence with sizes of the left atrial appendage closure device. In the present example, the information about sizes of the left atrial appendage is, for example, information including at least one selected from among: the maximum diameter, the minimum diameter, the mean diameter, the perimeter length, and the area of the left atrial appendage entrance part; the distance (a left atrial appendage distance) from the ultrasound wave transmission/reception surface of the ultrasound probe 1 to the left atrial appendage entrance part; and the distance (a left atrial appendage depth) from the left atrial appendage entrance part to an arbitrary left atrial appendage inner wall.

The program and the various types of data may be stored in the storage circuit 110 in advance, for example. Further, the program and the various types of data may be distributed as being stored in a non-transitory storage medium, for example, so as to be installed in the storage circuit 110 after being read from the non-transitory storage medium. Further, the storage circuit 110 may serve as an example of a storage unit according to the present embodiment.

The controlling circuit 111 is configured to comprehensively control operations in the entirety of the ultrasound diagnosis apparatus 100. For example, the controlling circuit 111 is configured to control the ultrasound scans, by controlling the ultrasound probe 1 via the transmission and reception circuit 101.

Further, the controlling circuit 111 is configured to control the position of an ultrasound scan cross-section, in order to obtain a two-dimensional image on the recommended cross-section calculated in the recommended cross-section position calculating process (explained later).

The NW interface 112 is connected to the external device 400 via the network NW, for example, and is configured to perform data communication with the external device 400.

For example, the external device 400 is a workstation configured to perform processes such as a post-processing process on various types of data generated by the ultrasound diagnosis apparatus 100, displaying ultrasound image data, and the like. For example, the external device 400 includes a processing circuit such as a processor, a storage device, a display device, an input device, and a NW interface connectable to the ultrasound diagnosis apparatus 100 via the network NW. Alternatively, the external device 400 may be a tablet terminal or the like.

In this situation, the B-mode processing circuit 103, the Doppler processing circuit 104, the image generating circuit 107, the display controlling circuit 108, and the controlling circuit 111 illustrated in FIG. 1 are realized by using a processor. For example, the storage circuit 110 has stored therein computer-executable programs defining the processes executed by these circuits. These circuits are configured to realize the functions corresponding to the programs, by reading and executing the programs from the storage circuit 110. Further, although the example was explained with reference to FIG. 1 in which the single storage circuit (the storage circuit 110) stores therein the programs corresponding to the processing functions, it is also acceptable to provide a plurality of storage circuits in a distributed manner, so that each of the circuits reads a corresponding program from one of the individual storage circuits.

In the above sections, the example was explained in which the "processor" is configured to read and execute the programs corresponding to the functions from the storage circuit 110; however, possible embodiments are not limited to this example. The term "processor" denotes, for example, a Central Processing Unit (CPU), a Graphics Processing Unit (GPU), or a circuit such as an Application Specific Integrated Circuit (ASIC) or a programmable logic device (e.g., a Simple Programmable Logic Device [SPLD], a Complex Programmable Logic Device [CPLD], or a Field Programmable Gate Array [FPGA]). When the processor is a CPU, for example, the processor is configured to realize the functions illustrated in FIGS. 1 and 2 by reading and executing the programs saved in the storage circuit 110. In contrast, when the processor is an ASIC, instead of having the programs saved in the storage circuit 110, the functions are directly incorporated in the circuit of the processor as a logic circuit. Further, the processors of the present embodiment do not each necessarily have to be structured as a single circuit. It is also acceptable to structure one processor by combining together a plurality of independent circuits so as to realize the functions thereof. Further, it is also acceptable to integrate two or more of the constituent elements illustrated in FIG. 1 and/or FIG. 2 (explained later) into one processor so as to realize the functions thereof.

Next, details of the image generating circuit 107 will be explained.

Figure 2:
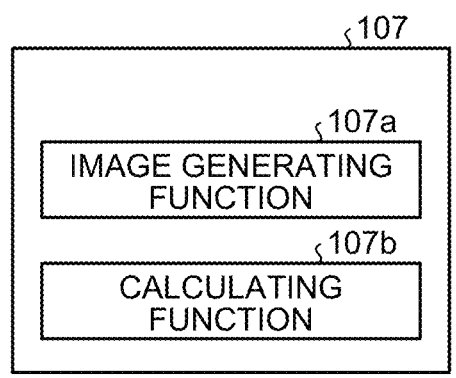
FIG. 2 is a diagram illustrating examples of functions of an image generating circuit according to the embodiment.

FIG. 2 is a diagram illustrating examples of functions of the image generating circuit 107 according to the embodiment. As illustrated in FIG. 2, the image generating circuit 107 includes an image generating function 107*a* and a calculating function 107*b*.

The image generating function 107*a* is configured to generate a three-dimensional model of the target site by using the obtained three-dimensional data. In other words, the image generating function 107*a* is configured to perform the shape estimation model generating process. More specifically, the image generating function 107*a* is configured to obtain, for example, a plurality of short-axis cross-section images of the left atrial appendage by using volume data related to the left atrial appendage. For example, by performing a segmentation process using a threshold value process, Artificial Intelligence (AI), or the like, the image generating function 107*a* is configured to search for the internal wall of the left atrial appendage from the obtained short-axis cross-section images of the left atrial appendage. The image generating function 107*a* is configured to generate the shape estimation model of the left atrial appendage serving as the three-dimensional model of the target site, by tracing and connecting points of the internal wall of the left atrial appendage obtained in the search. The shape estimation model of the left atrial appendage generated by the image generating function 107*a* is displayed on the display device 2 in a predetermined mode. The image generating function 107*a* is an example of an image generating unit.

Figure 3:
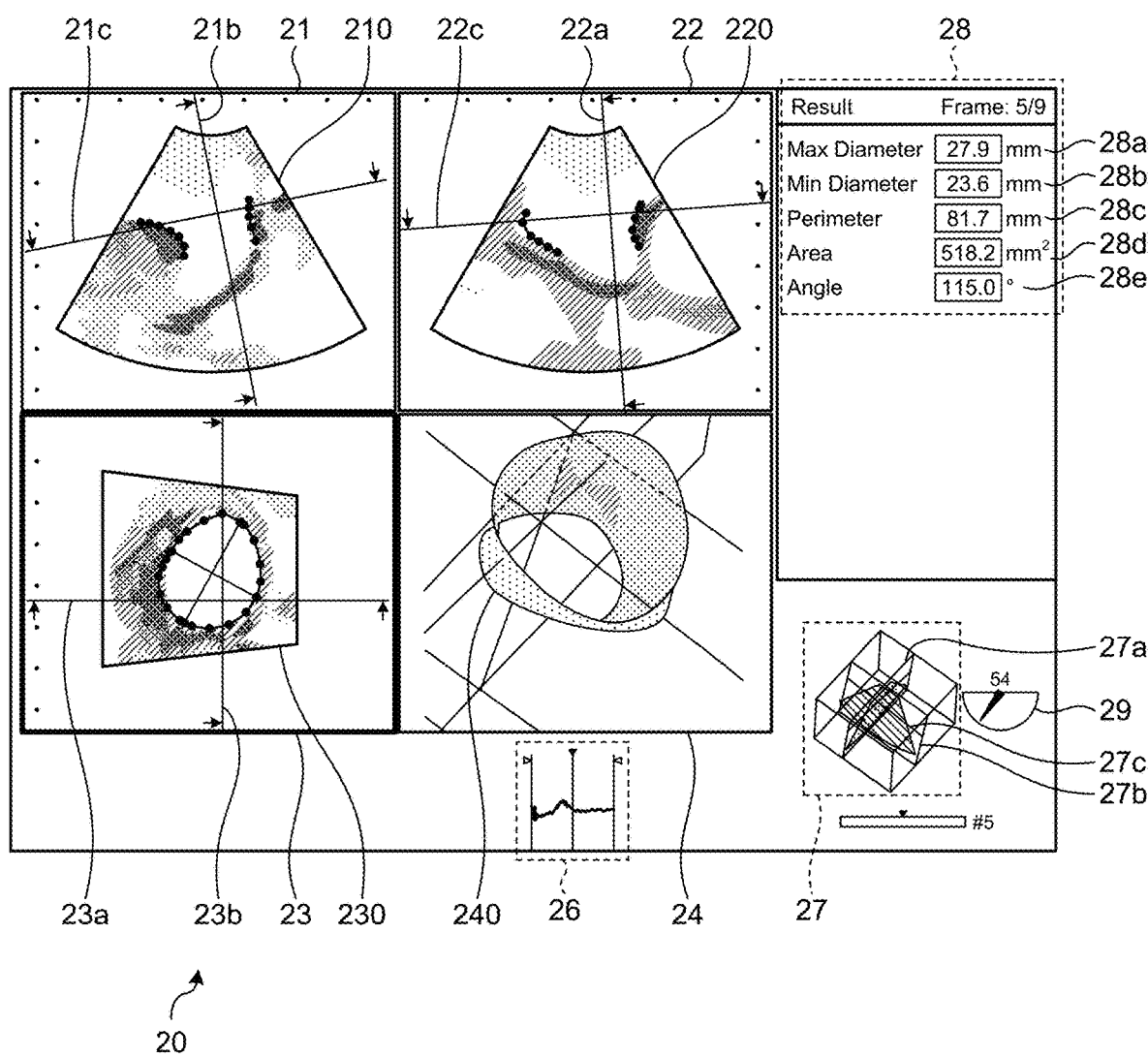
FIG. 3 is a drawing for explaining an example of a shape estimation model generating process performed by the image generating circuit according to the embodiment.

FIG. 3 is a drawing for explaining an example of the shape estimation model generating process performed by the image generating circuit according to the embodiment. FIG. 3 depicts an example of a display image 20 displayed on the display device 2 as a result of the shape estimation model generating process. As illustrated in FIG. 3, the display image 20 includes a cross-section A region 21 displaying a cross-section A image 210, a cross-section B region 22 displaying a cross-section B image 220, a cross-section C region 23 displaying a cross-section C image 230, a shape estimation model display region 24 displaying a shape estimation model 240, an electrocardiogram display region 26, a cross-section navigation information display region 27, a measurement value display region 28, and an ultrasound probe navigation information display region 29.

In the present example, cross-section A denotes a predetermined cross-section extending in the transmission/reception direction of the ultrasound wave (a raster line direction) and in the raster array direction. Cross-section B denotes another predetermined cross-section being orthogonal to cross-section A and extending in the raster line direction and the raster array direction. Cross-section C denotes yet another predetermined cross-section being orthogonal to the raster line direction and the raster array direction (i.e., being orthogonal to cross-section A and cross-section B). In the cross-section A region 21, straight lines 21*b* and 21*c* indicate the positions of the cross-section B image 220 and the cross-section C image 230, respectively. In the cross-section B region 22, straight lines 22*a* and 22*c* indicate the positions of the cross-section A image 210 and the cross-section C image 230, respectively. In the cross-section C region 23, straight lines 23*a* and 23*b* indicate the positions of the cross-section A image 210 and the cross-section B image 220, respectively. In the cross-section navigation information display region 27, cross-sections 27*a*, 27*b*, and 27*c* indicate the positions of, and the positional relationships among, the cross-section A image 210, the cross-section B image 220, and the cross-section C image 230 in the volume data. The ultrasound probe navigation information display region 29 indicates the position (the angle) of cross-section A at present.

The image generating function 107*a* is configured to obtain the cross-section C image 230, which is a short-axis cross-section image of the left atrial appendage, at a plurality of positions on a long axis of the left atrial appendage and to search for the internal wall of the left atrial appendage within the short-axis cross-section images. In FIG. 3, the internal wall of the left atrial appendage found in the search are indicated with the plurality of points in the cross-section C image 230. The image generating function 107*a* is configured to generate the shape estimation model 240 of the left atrial appendage by tracing and connecting the points of the internal wall of the left atrial appendage obtained in the search.

In this situation, the shape estimation model generating process by the image generating function 107*a* is repeatedly performed according to a volume rate of the ultrasound scan. Consequently, when the positions of any of cross-sections A, B, and C is updated, the shape estimation model 240 is also updated in a real-time manner in conjunction with the update.

Returning to the description of FIG. 2, the calculating function 107*b* is configured to calculate the position of at least one recommended cross-section to be set for the target site, on the basis of information about the size of the target site obtained by using the three-dimensional model. In other words, the calculating function 107*b* is configured to perform the target site size measuring process to obtain the information about the size of the left atrial appendage, by using the shape estimation model (or the ultrasound image used for generating the shape estimation model). The information about the size of the left atrial appendage obtained by the calculating function 107*b* is displayed on the display device 2 in a predetermined mode. The calculating function 107*b* is an example of a calculating unit.

Figure 4:
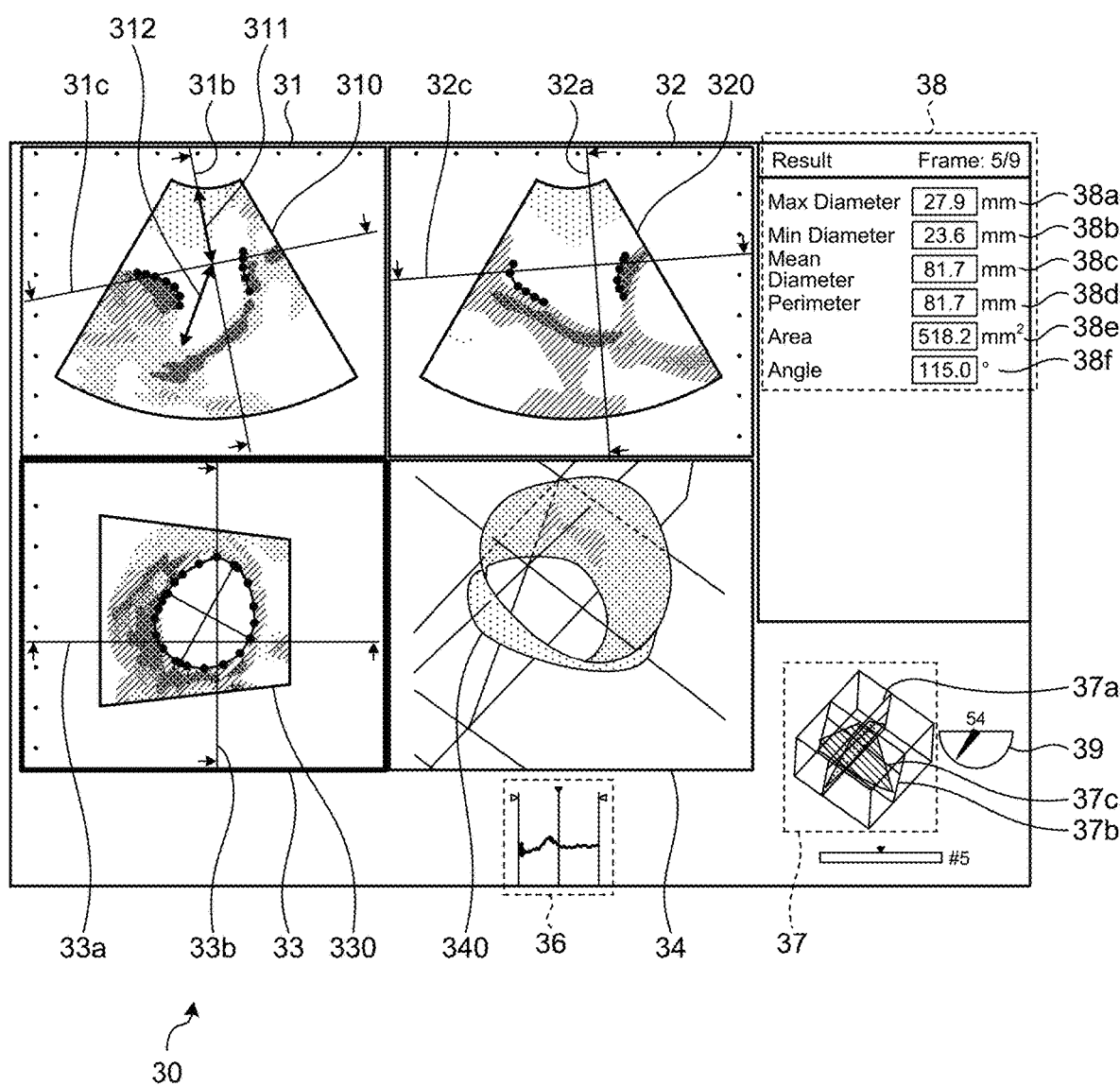
FIG. 4 is a drawing for explaining an example of a target site size measuring process performed by the image generating circuit according to the embodiment.

FIG. 4 is a drawing for explaining an example of the target site size measuring process performed by the image generating circuit according to the embodiment. FIG. 4 depicts an example of a display image 30 displayed on the display device 2 in the target site size measuring process.

In FIG. 4, similarly to the display image 20, the display image 30 includes a cross-section A region 31 displaying a cross-section A image 310, a cross-section B region 32 displaying a cross-section B image 320, a cross-section C region 33 displaying a cross-section C image 330, a shape estimation model display region 34 displaying a shape estimation model 340, an electrocardiogram display region 36, a cross-section navigation information display region 37, a measurement value display region 38, and an ultrasound probe navigation information display region 39. Further, straight lines 32*a* and 33*a* and a cross-section 27*a* indicate the position of cross-section A. Straight lines 31*b* and 33*b* and a cross-section 27*b* indicate the position of cross-section B. Straight lines 31*c* and 32*c* and a cross-section 27*c* indicate the position of cross-section C.

As illustrated in FIG. 4, by using the shape estimation model 340, the calculating function 107*b* is configured to measure a left atrial appendage distance 311 and a left atrial appendage depth 312 indicated in the cross-section A image 310. Further, by approximating the left atrial appendage to an ellipsoidal body and using the shape estimation model 340, the calculating function 107*b* is configured to measure the maximum diameter, the minimum diameter, the mean diameter, the perimeter length, and the area of the left atrial appendage entrance part indicated in the cross-section C image 330. Measurement results obtained by the calculating function 107*b* are displayed, within the measurement value display region 28 in FIG. 4, for example, as a maximum diameter 38*a*, a minimum diameter 38*b*, a mean diameter 38*c*, a perimeter length 38*d*, and an area 38*e* of the left atrial appendage entrance part.

Returning to the description of FIG. 2, the calculating function 107*b* is configured to perform the recommended cross-section position calculating process, by using the shape estimation model. More specifically, by approximating the left atrial appendage to an ellipsoidal body and using the shape estimation model, the calculating function 107*b* is configured to calculate, as the positions of the recommended cross-sections, the position of a cross-section including the maximum diameter and the position of a cross-section including the minimum diameter. The positions of the recommended cross-sections calculated by the calculating function 107*b* are displayed on the display device 2 in a predetermined mode.

Figure 5:
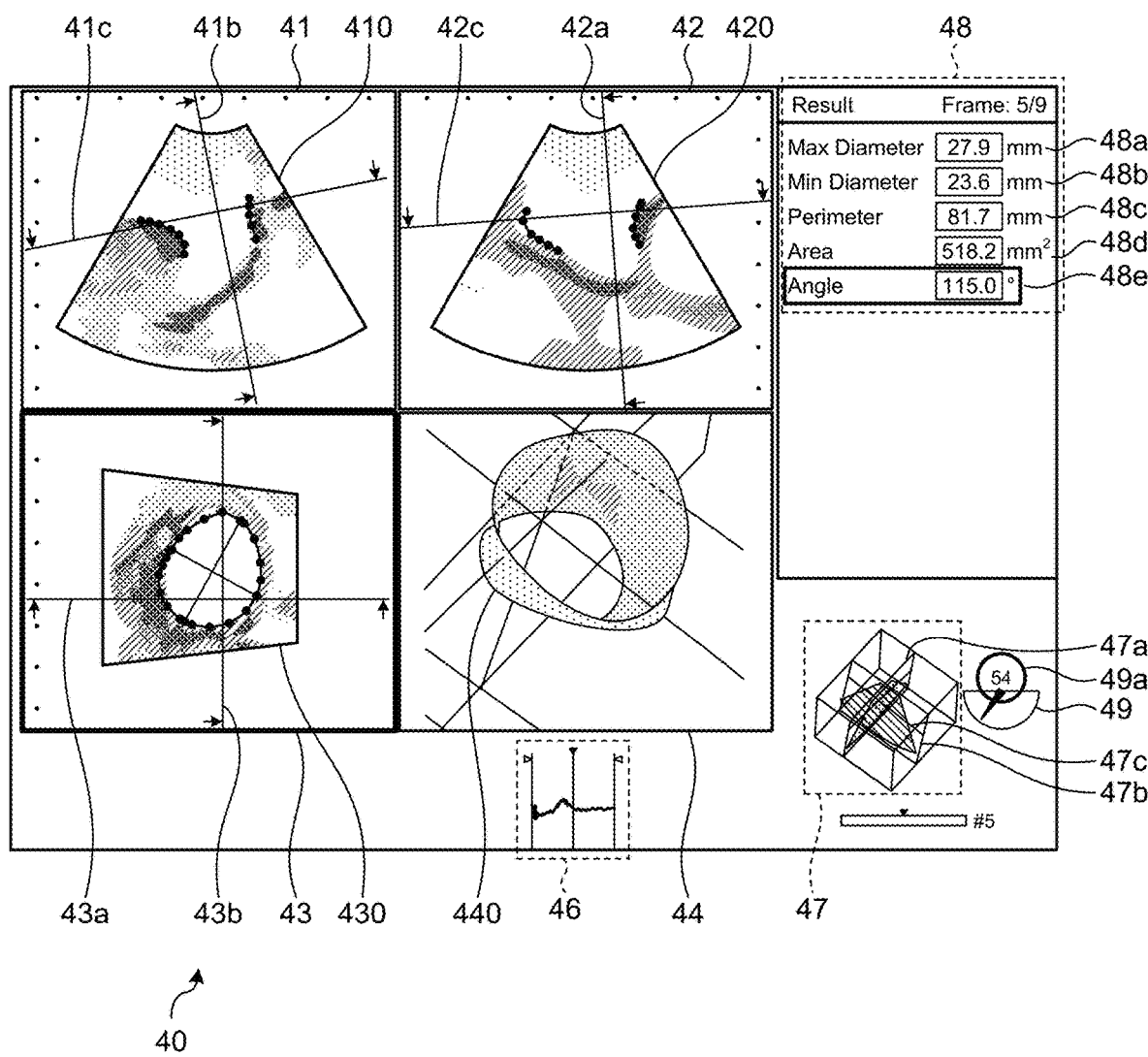
FIG. 5 is a drawing for explaining an example of a recommended cross-section position calculating process performed by the image generating circuit according to the embodiment.

FIG. 5 is a drawing for explaining an example of the recommended cross-section position calculating process performed by the image generating circuit according to the embodiment. FIG. 5 depicts an example of a display image 40 displayed on the display device 2 in the target site size measuring process.

In FIG. 5, similarly to the display image 20, the display image 40 includes a cross-section A region 41 displaying a cross-section A image 410, a cross-section B region 42 displaying a cross-section B image 420, a cross-section C region 43 displaying a cross-section C image 430, a shape estimation model display region 44 displaying a shape estimation model 440, an electrocardiogram display region 46, a cross-section navigation information display region 47, a measurement value display region 48, and an ultrasound probe navigation information display region 49. Further, straight lines 42*a* and 43*a* and a cross-section 47*a* indicate the position of cross-section A. Straight lines 41*b* and 43*b* and a cross-section 47*b* indicate the position of cross-section B. Straight lines 41*c* and 42*c* and a cross-section 47*c* indicate the position of cross-section C.

The calculating function 107*b* is configured to measure the position of the cross-section including the maximum diameter of the left atrial appendage entrance part and the position of the cross-section including the minimum diameter thereof indicated in the cross-section C image 330. The position of the cross-section including the maximum diameter of the left atrial appendage entrance part and the position of the cross-section including the minimum diameter thereof measured by the calculating function 107*b* are displayed within the cross-section C image 330 in FIG. 5, for example, as a straight line corresponding to the major axis and a straight lien corresponding to the short axis while the left atrial appendage entrance part is approximated to an ellipse.

Further, the calculating function 107b is configured to calculate the angle of the recommended cross-section from a reference position (a reference angle). The angle of the recommended cross-section from the reference position measured by the calculating function 107b is displayed within the measurement value display region 48 in FIG. 5, for example, as a recommended scan angle 48e (similarly indicated as a recommended scan angle 28e in FIG. 3 and as a recommended scan angle 38f in FIG. 4).

Further, as illustrated in FIG. 5, in the ultrasound probe navigation information display region 49, the angle 49a of cross-section A at present from the reference position is displayed. Accordingly, the operator is able to easily and promptly make visual recognition as to by how many degrees the present position (angle) of cross-section A needs to be rotated in order to set the position of cross-section A at the position of the recommended cross-section.

Further, FIG. 5 depicts the example in which the angle 48e of the recommended cross-section from the reference position is displayed side by side with the angle 49a of cross-section A at present from the reference position. In addition to or in place of these pieces of angle information, it is also possible to display angle information indicating by how many degrees a rotation needs to be made from the present position (angle) of cross-section A. The angle information indicating by how many degrees the rotation needs to be made from the present position (angle) of cross-section A serves as an example of the information about the difference between the position of the ultrasound scan cross-section at present and the position of at least one recommended cross-section.

Returning to the description of FIG. 2, the calculating function 107b is configured to perform the device size determining process on the basis of the result of the target site size measuring process. More specifically, the calculating function 107b is configured to determine the size of a left atrial appendage closure device to be used for treatment of the patient, by comparing the information about the size of the left atrial appendage obtained from the target site size measuring process and the device size table stored in the storage circuit 110. The size of the left atrial appendage closure device determined by the calculating function 107b is displayed on the display device 2 in a predetermined mode.

Next, flows in various types of aiding processes performed by the ultrasound diagnosis apparatus 100 according to the present embodiment configured as described above will be explained.

Figure 6:
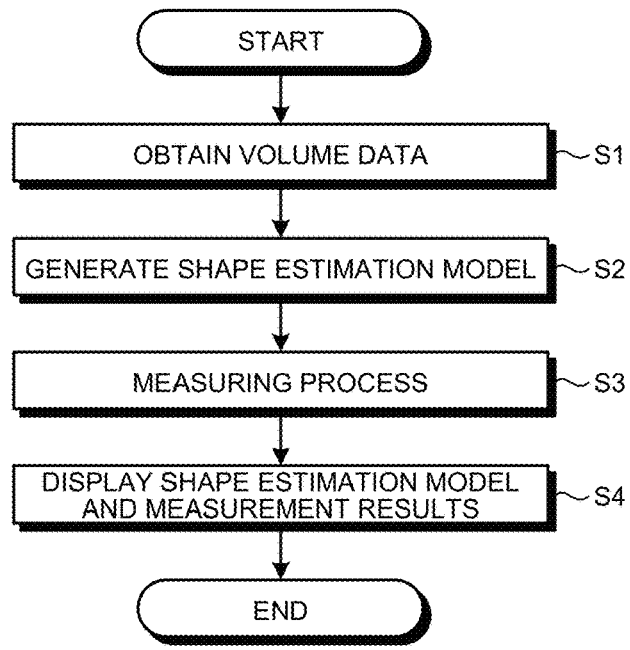
FIG. 6 is a flowchart illustrating an example of a flow in the target site size measuring process according to the embodiment.

The Target Site Size Measuring Process:

FIG. 6 is a flowchart illustrating an example of a flow in the target site size measuring process according to the embodiment. The target site size measuring process in the present example is performed, for instance, at the time of making a surgery plan or during an image diagnosis process before or after surgery. Further, the target site size measuring process in the present example is performed in synchronization with an electrocardiographic waveform so as to measure the size in a cardiac phase in which the left atrial volume is at a maximum, for example. Further, when the calculating process is performed in a plurality of temporal phases, the size is measured in a temporal phase in which the maximum diameter of the left atrial appendage entrance part is the largest.

As illustrated in FIG. 6, volume data related to the left atrial appendage is obtained by using the ultrasound probe 1 realized with a transesophageal probe (step S1).

The image generating function 107a included in the image generating circuit 107 generates a shape estimation model of the left atrial appendage (step S2).

The calculating function 107b included in the image generating circuit 107 performs the target site size measuring process by using the generated shape estimation model (step S3).

Figure 7:
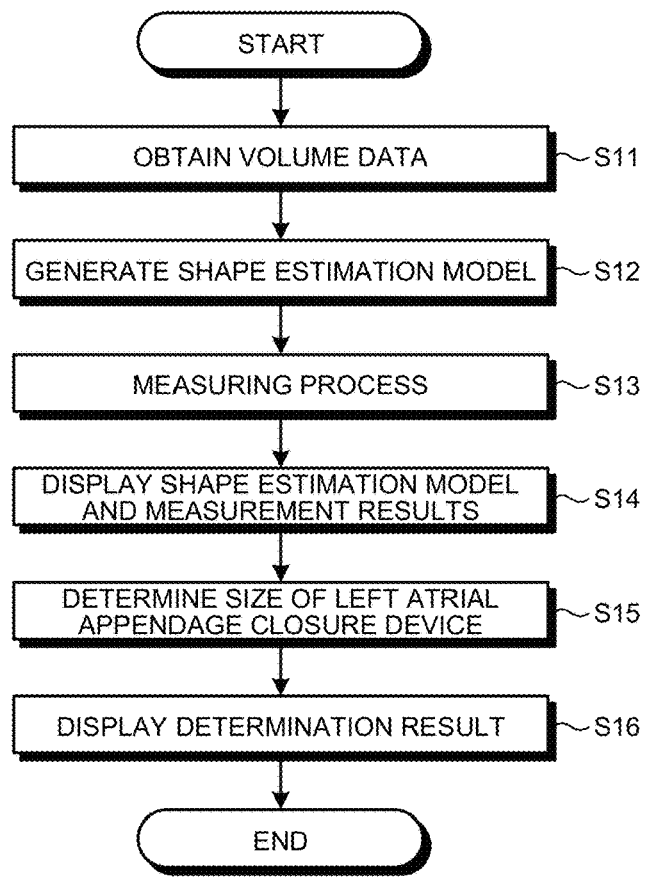
FIG. 7 is a flowchart illustrating an example of a flow in a device size determining process according to the embodiment.

The display controlling circuit 108 causes the display device 2 to display the generated shape estimation model and the information about the size of the left atrial appendage obtained as a measurement result (step S4). The device size determining process:

FIG. 7 is a flowchart illustrating an example of a flow in the device size determining process according to the embodiment. The device size determining process in the present example is performed, for instance, at the time of determining the size of a left atrial appendage closure device during surgery planning. Further, because the processes at steps S11 through S14 in FIG. 7 are the same as the processes at steps S1 through S4 in FIG. 6, the explanations thereof will be omitted.

The calculating function 107b included in the image generating circuit 107 performs the device size determining process on the basis of a result of the target site size measuring process (step S15).

The display controlling circuit 108 causes the display device 2 to display, in a predetermined mode, the size of the left atrial appendage closure device obtained as a determination result of the device size determining process (step S16).

A Left Atrial Appendage Closure Aiding Process:

FIG. 8 is a flowchart illustrating an example of a flow in a left atrial appendage closure aiding process including the recommended cross-section position calculating process according to the embodiment. The left atrial appendage closure aiding process in the present example is performed, for instance, at the time of monitoring the left atrial appendage in a real-time manner during a transcatheter left atrial appendage closure process. Further, because the processes at steps S21 through S24 in FIG. 8 are the same as the processes at steps S1 through S4 in FIG. 6, the explanations thereof will be omitted.

The calculating function 107b included in the image generating circuit 107 calculates scan cross-section positions to serve as recommended cross-section positions, by performing the recommended cross-section position calculating process on the basis of the result of the target site size measuring process (step S25).

The controlling circuit 111 performs the ultrasound transmission/reception controlling process on the basis of a scan cross-section position calculated as one of the recommended cross-section positions (step S26). In other words, to obtain a two-dimensional image of the scan cross-section position calculated as the one of the recommended cross-section positions, the controlling circuit 111 performs the ultrasound transmission/reception while controlling the position of the ultrasound scan cross-section. More specifically, from among the plurality of ultrasound transducer elements arranged two-dimensionally, the controlling circuit 111 selects multiple ultrasound transducer elements for two-dimensionally scanning the ultrasound scan cross-section position calculated as the one of the recommended cross-section positions. The controlling circuit 111 obtains the two-dimensional image corresponding to the recommended cross-section, by performing an ultrasound scan on the recommended cross-section while using the selected multiple ultrasound transducer elements.

The image generating circuit 107 generates a two-dimensional image corresponding to the scan cross-section position. The display controlling circuit 108 causes the display device 2 to display, in a predetermined mode, the two-dimensional image corresponding to the scan cross-section position (step S27).

The obtaining process and the generating and displaying process of the two-dimensional image corresponding to steps S26 and S27 are repeatedly performed with respect to each of the scan cross-section positions calculated at step S25.

For example, on the basis of whether a freeze operation from the ultrasound probe 1 or the input device 3 is present or not, the controlling circuit 111 determines whether or not the ultrasound scan is to be finished (step S28). When the controlling circuit 111 determines that the ultrasound scan is not to be finished (step S28: No), the processes at steps S21 through S27 are repeatedly performed. On the contrary, when the controlling circuit 111 determines that the ultrasound scan is to be finished (step S28: Yes), the left atrial appendage closure aiding process is ended.

In this situation, the processes at steps S21 through S27 may be performed with predetermined frequency (e.g., at least once) per heartbeat, for example, in synchronization with an electrocardiographic waveform.

Further, when the left atrial appendage closure process is performed altogether in one flow from when the size of the left atrial appendage closure device is determined, the device size determining process presented in FIG. 7 is performed at first, and the left atrial appendage closure aiding process presented in FIG. 8 is subsequently performed.

As explained above, the image generating function 107a included in the ultrasound diagnosis apparatus 100 according to the present embodiment is configured to generate the shape estimation model serving as the three-dimensional model of the left atrial appendage by using the obtained three-dimensional data related to the left atrial appendage. On the basis of the information about the size of the left atrial appendage entrance part obtained by using the shape estimation model, the calculating function 107b is configured to calculate the positions of the one or more recommended cross-sections to be set for the left atrial appendage. The display controlling circuit 108 is configured to cause the display device 2 to display the positions of the one or more recommended cross-sections.

Consequently, the operator is able to automatically understand the positions of the one or more recommended cross-sections to be set for the left atrial appendage. As a result, it is possible to realize the process of setting the desired imaged cross-sections for the target site, with reduced burdens and with a higher level of precision compared to those in the conventional example.

Further, the calculating function 107b included in the ultrasound diagnosis apparatus 100 according to the present embodiment is configured to calculate the information about the size including at least one selected from among the maximum diameter, the minimum diameter, the mean diameter, the perimeter length, and the area of the left atrial appendage entrance part in the shape estimation model and to further calculate the one or more recommended cross-sections to be set for the left atrial appendage, on the basis of the calculated information about the size.

Consequently, it is possible to accurately calculate the positions of the one or more recommended cross-sections to be set for the left atrial appendage, on the basis of the anatomical information.

The display controlling circuit 108 included in the ultrasound diagnosis apparatus 100 according to the present embodiment is configured to cause the display device 2 to display the position of the ultrasound scan cross-section at present and the positions of the one or more recommended cross-sections. The display controlling circuit 108 included in the ultrasound diagnosis apparatus 100 according to the present embodiment is also able to cause the display device 2 to display the information about the difference between the position of the ultrasound scan cross-section at present and the positions of the one or more recommended cross-sections.

Consequently, the operator is able to easily and promptly make visual recognition as to by how many degrees a rotation needs to be made from the present position (angle) of the ultrasound scan cross-section in order to set the present position of the ultrasound scan cross-section at the position of each of the recommended cross-sections. Consequently, it is possible to reduce the workload by aiding the practitioner performing the left atrial appendage closure process.

The controlling circuit 111 included in the ultrasound diagnosis apparatus 100 according to the present embodiment is configured to control the position of the ultrasound scan cross-section on the basis of the one or more recommended cross-sections. In other words, the controlling circuit 111 is configured to exercise control related to the ultrasound transmission/reception so that the position of the ultrasound scan cross-section is at the positions of the one or more recommended cross-sections.

Consequently, during the left atrial appendage closure process, for example, it is possible to display, in a real-time manner, the ultrasound image corresponding to each of the recommended cross-sections. Further, the ultrasound image corresponding to each of the recommended cross-sections is sequentially updated. By observing the displayed ultrasound images, the practitioner is able to perform manipulation while visually recognizing the accurate statuses. As a result, it is possible to make contribution to improving quality of the left atrial appendage closure process by aiding the practitioner.

The calculating function 107b included in the ultrasound diagnosis apparatus 100 according to the present embodiment is configured to determine the size of the left atrial appendage closure device on the basis of the information about the size of the left atrial appendage. The display controlling circuit 108 is configured to cause the display device 2 to display the determined size of the left atrial appendage closure device.

Consequently, on the basis of the measurement value accurately measured by using the recommended cross-sections, it is possible to accurately and automatically determine the size of the left atrial appendage closure device. As a result, it is possible to reduce burdens imposed on the medical doctor in the process of determining the size of the left atrial appendage closure device and to also make contribution to improving quality of the left atrial appendage closure process.

First Modification Example

With the ultrasound diagnosis apparatus 100 according to the above embodiment, the example was explained in which the positions of the recommended cross-sections are calculated, so as to subsequently perform the two-dimensional scans on the recommended cross-sections by changing the ultrasound scan region from the three-dimensional region to the two-dimensional regions.

Alternatively, it is also acceptable to keep the ultrasound scan region as a three-dimensional region after calculating the position of a recommended cross-section, so as to obtain an MPR image corresponding to the position of the recommended cross-section from volume data obtained in an ultrasound scan and to display the MPR image as a two-dimensional image corresponding to the recommended cross-section.

Second Modification Example

In the above embodiment, the example was explained in which the two-dimensional array probe is used as the ultrasound probe 1 realized with a transesophageal probe. Alternatively, as the ultrasound probe 1 realized with a transesophageal probe, it is also acceptable to use a mechanical ultrasound probe that makes it possible to scan a desired cross-section by rotating an ultrasound transducer element array arranged one-dimensionally.

In that situation, the controlling circuit 111 is configured to rotate the ultrasound transducer element array according to the calculated positions of the recommended cross-sections, so as to perform ultrasound transmission/reception with respect to the scan cross-sections corresponding to cross-section A and cross-section B.

With this configuration, it is possible to realize the same advantageous affects as those of the above embodiment, even by using the mechanical transesophageal probe.

Third Modification Example

In the above embodiment, the information about the size such as the maximum diameter is measured in the predetermined cardiac phase (e.g., the cardiac phase in which the left atrial volume is at a maximum), in synchronization with the electrocardiographic waveform. Alternatively, it is also acceptable to measure the information about the size by using the shape estimation model in a plurality of cardiac phases, in synchronization with an electrocardiographic waveform. In that situation, it is also possible to display an index value including information about temporal phases such as standard deviations of the maximum diameter, for example.

Fourth Modification Example

In the above embodiment, the example was explained in which the medical image diagnosis apparatus is the ultrasound diagnosis apparatus 100. In addition, the shape estimation model generating process, the target site size measuring process, the recommended cross-section position calculating process, and the device size determining process explained in the above embodiment are also applicable to other medical image diagnosis apparatuses such as X-ray Computed Tomography apparatuses (X-ray CT apparatuses), X-ray diagnosis apparatuses, and magnetic resonance imaging apparatuses. For example, it is possible to calculate the positions of the recommended cross-sections for a diagnosed target, by performing the same processes while using CT volume data obtained by an X-ray CT apparatus.

Further, it is possible to realize the shape estimation model generating process, the target site size measuring process, the recommended cross-section position calculating process, and the device size determining process according to the embodiment, not only with a medical image diagnosis apparatus, but also with a medical information processing apparatus such as a medical workstation. In that situation, the medical information processing apparatus is configured to obtain volume data taken by a medical image diagnosis apparatus, for example, and is capable of performing the shape estimation model generating process and the like according to the embodiment by using the obtained volume data. Further, it is also possible to transmit the information obtained in the shape estimation model generating process and the like according to the embodiment such as the device size, the measurement results, the positions of the recommended cross-sections, from the medical information processing apparatus to the medical image diagnosis apparatus and other terminals in a real-time manner.

Fifth Modification Example

In the above embodiment, to explain the specific examples, the left atrial appendage was used as an example of the diagnosed target. However, the shape estimation model generating process, the target site size measuring process, the recommended cross-section position calculating process, and the device size determining process according to the embodiment are applicable, not only to situations where the target site is the left atrial appendage, but also to situations where the target site is the interatrial septum or the mitral valve, for example.

According to at least one aspect of the embodiments described above, it is possible to realize the process of setting the desired imaged cross-sections for the target site with reduced burdens and with a higher level of precision compared to those in the conventional example.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical image diagnosis apparatus comprising a processing circuit configured:
to generate a three-dimensional model of a target site by using three-dimensional data related to the target site;
to calculate a position of at least one recommended cross-section to be set for the target site, on a basis of information about a size of the target site obtained by using the three-dimensional model; and
to cause a display device to display the position of said at least one recommended cross-section,
wherein
the target site is a left atrial appendage,
the processing circuit is further configured to calculate the information about the size including at least one selected from among a maximum diameter, a minimum diameter, a perimeter length, and an area of the target site on a short-axis cross-section set in the three-dimensional model, and
the processing circuit is further configured to calculate the position of said at least one recommended cross-section to be set for the left atrial appendage, on the basis of the calculated information about the size.

2. The medical image diagnosis apparatus according to claim 1, wherein the medical image diagnosis apparatus is an ultrasound diagnosis apparatus, and the processing circuit is further configured to calculate the position of said at least one recommended cross-section, as an ultrasound scan cross-section scanned by using a transesophageal probe.

3. The medical image diagnosis apparatus according to claim 2, wherein the processing circuit is further configured to cause the display device to display a position of an ultrasound scan cross-section at present and the position of said at least one recommended cross-section.

4. The medical image diagnosis apparatus according to claim 2, wherein the processing circuit is further configured to cause the display device to display information about a difference between a position of an ultrasound scan cross-section at present and the position of said at least one recommended cross-section.

5. The medical image diagnosis apparatus according to claim 2, wherein the processing circuit is further configured to cause the display device to display a difference angle between a position of an ultrasound scan cross-section at present and the position of said at least one recommended cross-section.

6. The medical image diagnosis apparatus according to claim 1, wherein the processing circuit is further configured to control a position of an ultrasound scan cross-section, on a basis of the position of said at least one recommended cross-section.

7. The medical image diagnosis apparatus according to claim 1, wherein the processing circuit is further configured to determine a size of a medical device to be placed for the target site, on the basis of the information about the size, and the processing circuit is further configured to cause the display device to display the determined size of the medical device.

8. The medical image diagnosis apparatus according to claim 1, wherein the target site is a left atrial appendage, and by approximating the left atrial appendage to an ellipsoidal body and using a shape estimation model, the processing circuit is further configured to calculate a position of a cross-section including a maximum diameter and a position of a cross-section including a minimum diameter each as the position of the recommended cross-section.

9. A medical information processing apparatus comprising a processing circuit configured:

to generate a three-dimensional model of a target site by using three-dimensional data related to the target site;

to calculate a position of at least one recommended cross-section to be set for the target site, on a basis of information about a size of the target site obtained by using the three-dimensional model; and to cause an output device to output the position of said at least one recommended cross-section, wherein the target site is a left atrial appendage, the processing circuit is further configured to calculate the information about the size including at least one selected from among a maximum diameter, a minimum diameter, a perimeter length, and an area of the target site on a short-axis cross-section set in the three-dimensional model, and the processing circuit is further configured to calculate the position of said at least one recommended cross-section to be set for the left atrial appendage, on the basis of the calculated information about the size.

10. A medical information processing method comprising:

generating a three-dimensional model of a target site by using three-dimensional data related to the target site;

calculating a position of at least one recommended cross-section to be set for the target site, on a basis of information about a size of the target site obtained by using the three-dimensional model; and causing an output device to output the position of said at least one recommended cross-section, wherein the target site is a left atrial appendage, the method further comprises calculating the information about the size including at least one selected from among a maximum diameter, a minimum diameter, a perimeter length, and an area of the target site on a short-axis cross-section set in the three-dimensional model, and the method further comprises calculating the position of said at least one recommended cross-section to be set for the left atrial appendage, on the basis of the calculated information about the size.

* * * * *